US00PP22497P2

(12) United States Plant Patent
Verschoor

(10) Patent No.: US PP22,497 P2
(45) Date of Patent: Feb. 14, 2012

(54) ***VERONICA* PLANT NAMED 'BLUE EXPLOSION'**

(50) Latin Name: ***Veronica* sp.**
Varietal Denomination: Blue Explosion

(76) Inventor: Jan Verschoor, Haarlem (NL)

( * ) Notice: Subject to any disclaimer, the term of this patent is extended or adjusted under 35 U.S.C. 154(b) by 0 days.

(21) Appl. No.: 12/931,498

(22) Filed: Feb. 2, 2011

(51) Int. Cl.
*A01H 5/00* (2006.01)

(52) U.S. Cl. ..... Plt./251

(58) Field of Classification Search ..... Plt./251
See application file for complete search history.

*Primary Examiner* — Kent L Bell
(74) *Attorney, Agent, or Firm* — Jondle & Associates, P.C.

(57) ABSTRACT

A *Veronica* plant particularly distinguished by a compact, well-branched plant habit, strong stems, strongly-branched, compact inflorescences, a very floriferous blooming habit with re-blooming and easy to grow a strong and well-developed plant in one season, is disclosed.

2 Drawing Sheets

Genus and species: *Veronica* sp.
Variety denomination: 'Blue Explosion'.

BACKGROUND OF THE NEW PLANT

The present invention comprises a new and distinct variety of *Veronica,* botanically known as *Veronica* sp., and hereinafter referred to by the variety name 'Blue Explosion'. 'Blue Explosion' was developed through a cross conducted in the summer of 2006 between the female, an un-named proprietary *Veronica* sp. seedling (unpatented) and the male parent, an un-named proprietary *Veronica* sp. seedling (unpatented) in Haarlem, The Netherlands. 'Blue Explosion' was selected as a single plant in June 2007 and was first propagated in summer 2007 via softwood cuttings.

'Blue Explosion' has been propagated for approximately 4 generations via softwood cuttings and has been found to retain its distinctive characteristics through successive asexual propagations via softwood cuttings in Haarlem, The Netherlands.

Plant Breeder's Rights for this variety have not been applied for. 'Blue Explosion' has not been made publicly available or sold more than one year prior to the filing date of this application.

SUMMARY OF THE INVENTION

The following are the most outstanding and distinguishing characteristics of this new cultivar when grown under normal horticultural practices in Haarlem, The Netherlands.

1. A compact, well-branched plant habit;
2. Strong stems;
3. Strongly-branched, compact inflorescences;
4. A very floriferous blooming habit with violet buds and re-blooming; and
5. Easy to grow a strong and well-developed plant in one season.

DESCRIPTION OF THE PHOTOGRAPHS

This new *Veronica* plant is illustrated by the accompanying photographs which show blooms, buds, and foliage of the plant in full color; the colors shown are as true as can be reasonably obtained by conventional photographic procedures. The photographs are of two-year-old plants grown in Haarlem, The Netherlands in July 2010.

DESCRIPTION OF THE NEW CULTIVAR

Figure 1:
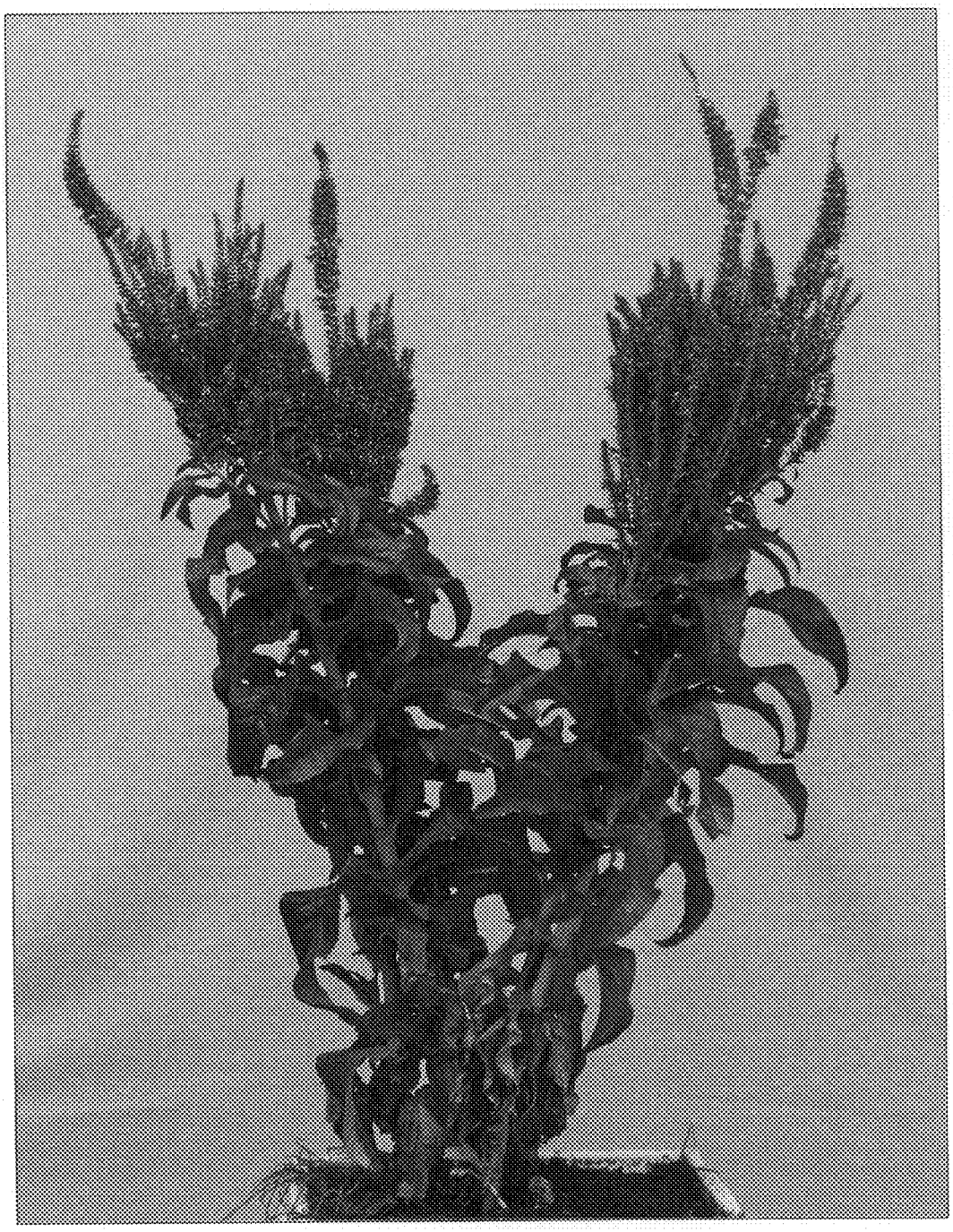
FIG. 1 shows a whole plant, including leaves, buds and inflorescence.
Figure 2:
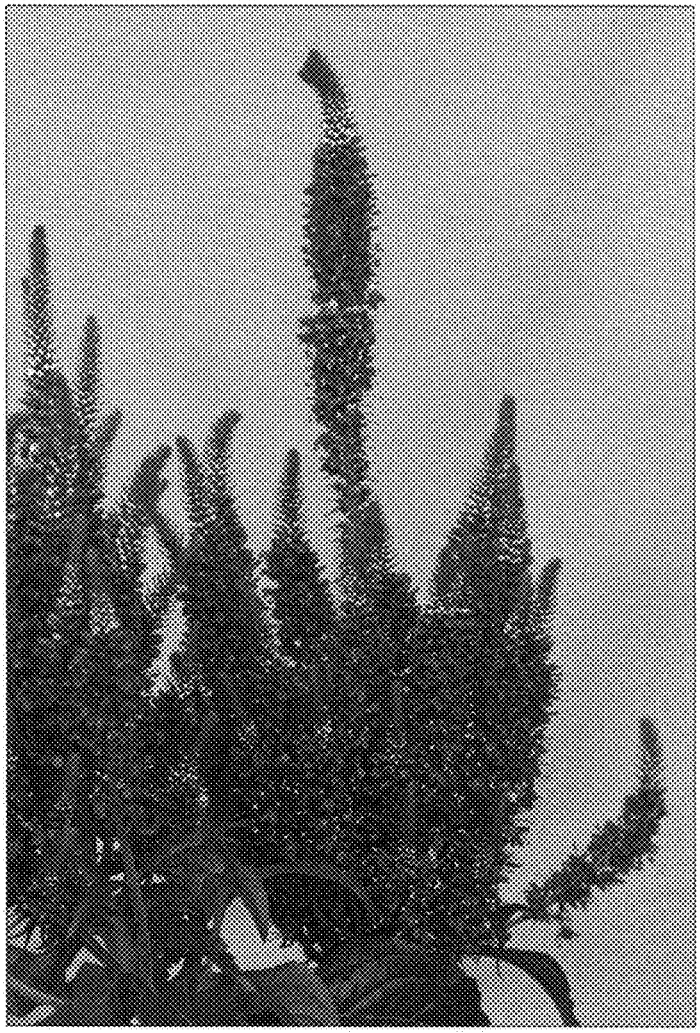
FIG. 2 shows a close-up of the inflorescence.
Figure 3:
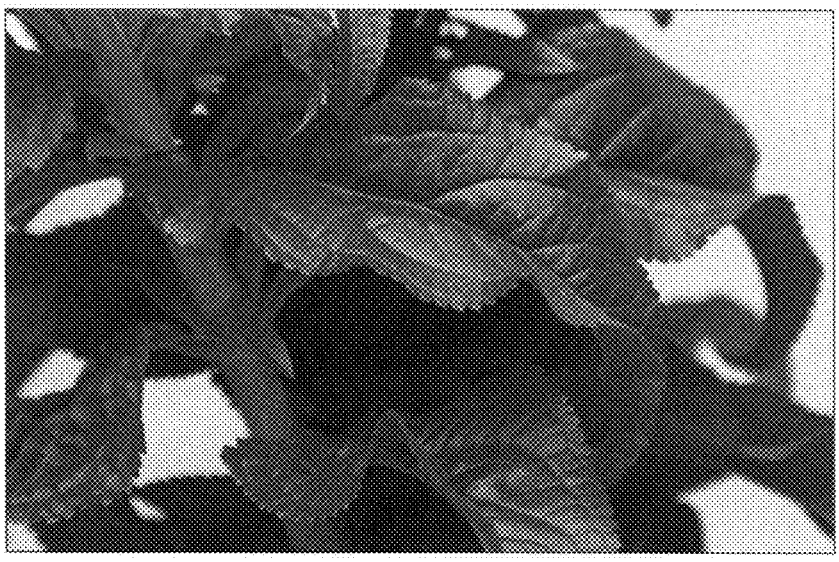
FIG. 3 shows a close-up of a mature leaf.

The following detailed descriptions set forth the distinctive characteristics of 'Blue Explosion'. The data which define these characteristics were collected from asexual reproductions carried out in Haarlem, The Netherlands. The plant history was taken on two-year-old plants grown outdoors in Haarlem, The Netherlands in July 2010. Color readings were taken under natural light. Color references are primarily to The R.H.S. Colour Chart of The Royal Horticultural Society of London (R.H.S.) (2007 edition).

DETAILED BOTANICAL DESCRIPTION OF THE NEW PLANT

Classification:
- *Family.*—Scrophulariaceae.
- *Botanical name.*—*Veronica* sp.
- *Denomination.*—'Blue Explosion'.

Parentage:
- *Female parent.*—An un-named, proprietary *Veronica* sp. seedling (unpatented).
- *Male parent.*—An un-named, proprietary *Veronica* sp. seedling (unpatented).

Growth:
- *Plant habit.*—Upright.
- *Life cycle.*—Herbaceous Perennial.
- *Shape.*—Inverted triangle.
- *Growth rate.*—In the spring, about 8.0 cm per month.
- *Vigor.*—Moderate.
- *Plant height* (*from top of soil*).—64.4 cm.
- *Plant width* (*horizontal plant diameter*).—43.0 cm.
- *Time to produce a finished flowering plant.*—About 4 months.

*Branching description.*—Freely branching from the base.

*Basal branching.*—Present.

*Average number of lateral branches per plant.*—5 main stems.

*Lateral branch length* (*excluding the inflorescence*).—39.6 cm.

*Lateral branch diameter.*—7.0 mm.

*Internode length.*—3.4 cm.

*High temperature tolerance.*—At least tolerant to temperatures up to 35 degrees Celsius.

*Low temperature tolerance.*—At least tolerant to temperatures as low as USDA Zone 4.

Stem:

*Appearance.*—Rounded and slightly glossy.

*Aspect.*—Rounded.

*Strength.*—Strong.

*Color.*—RHS 144A and RHS 144B (Green).

*Pubescence.*—Densely pubescent; average length of hairs is 0.5 mm and greyed-white (the pubescence is too small to be accurately measured by R.H.S. but is close to RHS 156D).

Leaves:

*Durability of foliage to stress.*—High.

*Arrangement and type.*—Opposite, single.

*Quantity of leaves per lateral branch.*—24 (12 pairs).

*Shape.*—Ovate, sinuate and curved.

*Apex.*—Acute.

*Base.*—Cordate.

*Margin.*—Serrate.

*Length.*—11.8 cm.

*Width.*—4.8 cm.

*Texture.*—Upper surface is moderately glossy; lower surface is slightly glossy and smooth.

*Pubescence.*—Upper surface is sparsely covered with very short hairs that are 0.2 mm in length, and greenish-white (hairs are too small to be accurately measured with R.H.S.). Lower surface is smooth except for main vein, which is sparsely covered with very short hairs that are 0.3 mm in length and greenish-white (hairs are too small to be accurately measured with R.H.S.).

*Venation pattern.*—Pinnate.

*Venation color.*—Upper surface: RHS 143C (Green). Lower surface: RHS 144B and RHS 144C (Yellow-green).

*Immature leaf color.*—Upper surface: RHS 143A (Green). Lower surface: RHS 144A (Yellow-green).

*Mature leaf color.*—Upper surface: RHS N137C (Green). Lower surface: RHS 147B (Yellow-green).

*Petiole.*—Shape: V-shaped. Length: 1.5 cm. Diameter: Average width is 4.0 mm. Color: RHS 144B (Yellow-Green).

Inflorescence:

*Arrangement.*—Compound terminal raceme.

*Height.*—28.1 cm.

*Width.*—11.9 cm.

*Quantity of flowers per inflorescence.*—Primary racemes average approximately 300; secondary racemes average approximately 125; each inflorescence holds an average of 24 secondary racemes.

*Flowering habit* (*length of flowering season*).—Continuously from July to late September.

*Quantity of flowers per lateral stem.*—1,100.

*Quantity of flower buds per lateral stem.*—2,200.

*Quantity of flowers and buds per plant.*—16,000.

*Time to flower.*—Approximately 8 months when field-grown.

*Fragrance.*—Absent.

*Rate of flower opening.*—Of the terminal raceme, approximately 20% are open at any given time; of the secondary racemes, approximately 35% are open at any given time.

Flower buds:

*Length.*—4.0 mm.

*Diameter.*—2.0 mm.

*Shape.*—Oblong.

*Rate of opening.*—Approximately 20% opens at once; all flowers have opened in approximately 8 weeks.

*Color.*—RHS N88C (Violet) and RHS 144A (Yellow-green) at the base (immature. calyx).

Flowers:

*Aspect.*—Outward.

*Type.*—Campanulate.

*Lastingness of flowers on the plant.*—Approximately 7 days.

*Diameter.*—7.0 mm.

*Depth.*—5 0 mm.

*Persistent or self-cleaning.*—Self-cleaning.

*Petals.*—Appearance: Dull, smooth. Quantity per flower: 4. Arrangement: Campanulate, lower 30% or 40% fused. Shape: Obovate, lower petal narrow obovate. Apex: Obtuse. Base: Fused. Margin: Entire. Length: 6.0 mm and lower petals average 5.0 mm. Width: 2.5 mm and upper petals average 2.0 mm.

*Color when opening* (*both surfaces*).—RHS 90B (Violet-blue).

*Color when fully opened* (*both surfaces*).—RHS 90C (Violet-blue); fades to RHS 90A (Violet-blue).

*Calyx.*—Shape: Rotate. Length: 3.0 mm. Diameter: 2.0 mm.

*Sepals.*—Arrangement: Rotate. Texture: Dull, smooth. Quantity per flower: 4. Shape: Narrow ovate. Apex: Acute. Base: Cuneate, lower 5% fused. Margin: Entire. Length: 3.0 mm. Width: 1.0 mm. Color: Immature (both surfaces): RHS 144A (Yellow-green). Mature (both surfaces): RHS 137B and RHS 137C (Green); base is lighter, RHS 143B and RHS 143C.

*Peduncle.*—Length: 27.8 cm. Diameter: 3.0 mm. Color: RHS 143B and RHS 143C (Green). Angle: Primary racemes are straight upright, secondary racemes are at an average angle of 30 degrees. Strength: Strong.

*Pedicel.*—Length: 1.0 mm. Diameter: 0.5 mm. Angle: 60 degrees. Strength: Moderately strong. Color: RHS 144A (Yellow-green).

Reproductive organs:

*Stamens.*—Number: 2. Filament: Length: 9.0 mm. Color: RHS 94B (Violet-blue). Anthers: Shape: Dorsifixed, sagittate. Width: 1.7 mm. Color: RHS N77A (Purple). Pollen amount: Moderate to high. Pollen color: RHS 4D (Yellow).

*Pistils.*—Number: 1. Pistil length: 6.0 mm. Stigma: Color: RHS N92B and RHS N92C (Violate-blue). Shape: Clavate. Style: Color: RHS 93B (Violet-blue). Length: 5.5 mm.

*Ovary.*—Color: RHS 144B (Yellow-green).

Fruit/seed set: No fruit or seeds observed.

Disease and insect resistance: No more susceptible or resistant than other *Veronica* varieties.

COMPARISON WITH PARENTAL AND COMMERCIAL VARIETY

'Blue Explosion' differs from the female parent, a proprietary un-named *Veronica* plant (unpatented) in that 'Blue Explosion' has more strongly branched and compact inflorescences than the female parent. Additionally, 'Blue Explosion' has a deep violet-blue flower color whereas the female parent has lighter blue flowers.

The male parent of 'Blue Explosion' is no longer available for comparison.

'Blue Explosion' differs from the commercial variety 'Pink Panther' (U.S. Plant Pat. No. 16,311) in that 'Blue Explosion' has a violet flower bud color and violet-blue flowers, whereas 'Pink Panther' has red-purple flower buds and flowers.

I claim:

1. A new and distinct variety of *Veronica* plant as described and shown herein.

* * * * *